US009034382B2

(12) United States Patent
Li et al.

(10) Patent No.: US 9,034,382 B2
(45) Date of Patent: May 19, 2015

(54) OSELTAMIVIR PHOSPHATE GRANULE AND PREPARATION METHOD THEREOF

(75) Inventors: Song Li, Beijing (CN); Wu Zhong, Beijing (CN); Junhai Xiao, Beijing (CN); Yunde Xie, Beijing (CN); Xingzhou Li, Beijing (CN); Hao Cui, Beijing (CN); Zhibing Zheng, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 709 days.

(21) Appl. No.: 12/225,935

(22) PCT Filed: Aug. 11, 2006

(86) PCT No.: PCT/CN2006/002043
§ 371 (c)(1),
(2), (4) Date: Nov. 19, 2008

(87) PCT Pub. No.: WO2007/112619
PCT Pub. Date: Oct. 11, 2007

(65) Prior Publication Data
US 2009/0176877 A1 Jul. 9, 2009

(30) Foreign Application Priority Data

Apr. 4, 2006 (CN) .......................... 2006 1 0066995

(51) Int. Cl.
A61K 9/14 (2006.01)
A61K 31/215 (2006.01)
A61K 9/16 (2006.01)
A61K 9/00 (2006.01)

(52) U.S. Cl.
CPC ............... A61K 31/215 (2013.01); A61K 9/141 (2013.01); A61K 9/0056 (2013.01); A61K 9/0095 (2013.01); A61K 9/1623 (2013.01); A61K 9/1635 (2013.01); A61K 9/1652 (2013.01)

(58) Field of Classification Search
None
See application file for complete search history.

(56) References Cited

U.S. PATENT DOCUMENTS 5,607,697 A * 3/1997 Alkire et al. .................. 424/495
5,972,668 A 10/1999 Georg et al.
6,534,087 B2 3/2003 Busson et al.
7,074,431 B2 7/2006 Busson et al.
2002/0018812 A1 2/2002 Busson et al.
2003/0039614 A1 2/2003 Busson et al.
2004/0062801 A1* 4/2004 Faour et al. .................. 424/468
2004/0198838 A1* 10/2004 Alles et al. .................. 514/651
2006/0134205 A1 6/2006 Busson et al.
2009/0176877 A1 7/2009 Li et al.
2010/0222427 A1 9/2010 Kubota et al.

FOREIGN PATENT DOCUMENTS

| CN | 1438880 A | 8/2003 |
|---|---|---|
| EP | 1 987 825 A1 | 11/2008 |
| JP | 10-502114 | 2/1998 |
| JP | 2005-60265 | 3/2005 |
| JP | 2009-532390 | 9/2009 |
| WO | WO 2007/097325 A1 | 8/2007 |

OTHER PUBLICATIONS

Oo et al., "Pharmacokinetics and Dosage Recommendations for an Oseltamivir Oral Suspension for the Treatment of Influenza in Children", PaediatrDrugs, 2001, vol. 3., issue 3, pp. 229-236.*
International Search Report, dated Jan. 11, 2007, corresponding to PCT/CN2006/002043.
Notice of Allowance dated Nov. 12, 2010, with partial English translation, for corresponding Chinese Patent Application No. 200610066995.7.
Office Action dated Jun. 11, 2010, with partial English translation, for corresponding Chinese Patent Application No. 200610066995.7.
Office Action dated Sep. 4, 2009, with partial English translation, for corresponding Chinese Patent Application No. 200610066995.7.
Office Action dated Mar. 1, 2010, with partial English translation, for corresponding Chinese Patent Application No. 200610066995.7.
Examination Report dated Aug. 7, 2013 issued in corresponding European Patent Application No. 06 775 361.6, 5pp.
Extended European Search Report for corresponding EP Application No. 06775361.6, dated Nov. 12, 2012, 6pp.
Emea; "Tamiflu: EPAR—Scientific Discussion"; Tamiflu oseltamivir European public assessment report: Assessment history; Oct. 21, 2005, 25pp.
Office action for corresponding Japanese Patent Application No. 2009-503391, dated Apr. 17, 2012, 4pp.
Tamiflu Dry Syrup 3%; Anti-influenza medicine; 3pp.
Office action for corresponding Japanese Patent Application No. 2009-503391, dated Sep. 4, 2012.
Tamiflu; 2005; pp. 1-6.(Japanese Language).
Japanese Language Ingredients, 1994, pp. 32, 99, 100, 124-126, and 138.
Japanese Language article, 1971, pp. 50-55.

* cited by examiner

Primary Examiner — Jeffrey S Lundgren
Assistant Examiner — Stephanie Springer
(74) Attorney, Agent, or Firm — Christie, Parker & Hale, LLP

(57) ABSTRACT

The present invention relates to an oseltamivir phosphate granule and preparation method thereof. The said granule comprises 1.97-19.8 wt. % oseltamivir phosphate, 75.0-97.5 wt. % diluent, 0.1-5.0 wt. % binder, optionally 1.0-5.0 wt. % edible flavoring essence, sweetener and/or edible pigment. It is prepared by using 30-55 v/v % aqueous ethanol solution as moistening agent. The granules prepared by the formulation and method according to the present invention have good uniformity and stability and are water-soluble. The administration dosage of the granules can be conveniently selected based on the age and body weight of patients. The oseltamivir phosphate granule is suitable for administering to old people, children and flu gravis patients and those patients that swallow inconveniently or difficulty. The preparation of the granule is simple and low in production cost.

12 Claims, No Drawings

OSELTAMIVIR PHOSPHATE GRANULE AND PREPARATION METHOD THEREOF

CROSS REFERENCE TO RELATED APPLICATION

This application is National Phase Patent Application and claims the priority of International Application Number PCT/CN2006/002043, filed on Aug. 11, 2006, which claims priority of Chinese Patent Application Number 200610066995.7, filed on Apr. 4, 2006.

TECHNICAL FIELD

The present invention relates to oseltamivir phosphate granules and preparation method thereof.

BACKGROUND ART

Neuramidinase (NA) inhibitor is an anti-flu virus drug that has been developed recently. As a recently developed NA inhibitor, oseltamivir phosphate is effective to type A and B flu virus and has advantages of anti-drug fast, good tolerance of patient and high safety, and is used for the prevention and treatment of flu. oseltamivir phosphate is a therapeutic drug for preventing and controlling pandemic of flu used by World Health Organization and Chinese Ministry of Public Health, and also a drug reserved for national strategy to prevent and control pandemic of flu in China and other countries in the world.

At present, commercial oseltamivir preparation form in China is capsule, its unit dose is 98.5 mg/granule (which contain oseltamivir 75 mg), according to body weight-dose table recommended to children over 1 year old, oseltamivir phosphate is taken in a dose as listed as follows:

| Body weight | Recommended dose (taken for 5 days) |
| --- | --- |
| ≤15 kg | 30 mg, twice per day |
| >15-23 kg | 45 mg, twice per day |
| >23-40 kg | 60 mg, twice per day |
| >40 kg | 75 mg, twice per day |

Clearly, due to large dose, the capsule cannot be exactly administered to Children patients especially lower age children, and thereby the safety of administration cannot be guaranteed; on the other hand, since old people, children and flu gravis patients swallow inconveniently or difficulty, capsule dosage form is not suitable for these special human. Therefore, it is necessary to develop new dosage form of oseltamivir phosphate suitable for old people, children and flu gravis patients.

SUMMARY OF THE INVENTION

The inventor has developed oseltamivir phosphate granules having a plurality of advantages; for example, granules are water soluble, which can be taken after mixing with water, and thereby suitable for children and patients that are difficult to swallow capsules. The administration dose can be conveniently selected according to the age and body weight of patients. Moreover, the preparation is simple and low cost.

Hence, the present invention at one aspect relates to oseltamivir phosphate granules. Said granules comprise oseltamivir phosphate, at least one diluent, at least one binder and optionally edible flavouring essence, sweetener and/or edible pigment.

Particularly, the oseltamivir phosphate granules according to the present invention comprise 1.97-19.8 wt. % oseltamivir phosphate, 75.0-97.5 wt. % diluent, 0.1-5.0 wt. % binder, and optionally 1.0-5.0 wt. % edible flavouring essence, sweetener and/or edible pigment. The sum of various ingredients is equal to or less than 100%.

The present invention at another aspect provides a method for the preparation of oseltamivir phosphate granules, which comprises the steps of mixing oseltamivir phosphate, diluent, binder and optionally edible flavoring essence, sweetener and/or edible pigment, preparing soft material, passing through sieve, pelletizing, and finishing granules.

According to one embodiment of the present invention, oseltamivir phosphate granules per gram comprise 0.0197-0.198 g oseltamivir phosphate, and diluent, binder and optionally edible flavoring essence, sweetener and/or edible pigment.

According to another embodiment of the present invention, the oseltamivir phosphate granules of the present invention comprise:

Oseltamivir phosphate 1.97-19.8 wt. %
Diluent 75.0-97.5 wt. %
Binder 0.1-5.0 wt. %
Optionally 1.0-5.0 wt. % edible flavouring essence, sweetener and/or edible pigment.

The sum of the various ingredients is equal to or less than 100%.

According to further embodiment of the present invention, oseltamivir phosphate granules per unit dose contain 15-150 mg of oseltamivir, as active ingredient, for example, per unit dose contains 15 mg, 25 mg, 30 mg, 45 mg, 60 mg, 75 mg or 90 mg of oseltamivir, preferably 15 mg and 25 mg of oseltamivir.

The granules of the present invention are prepared into a soft material with 30-55 v/v %, preferably 40 v/v % of ethanol aqueous solution as wetting agent. Therefore, the obtained granules have appropriate degree of tightness, good fluidity, exact package amount, uniform content, and high release degree.

According to the present invention, the diluent used in oseltamivir phosphate granules is selected from one or two of powdered sugar, dextrin, sorbitol. Said powdered sugar includes but is not limited sucrose, glucose, Aspartame, Steviosin, etc. sugar in common sense; said diluent can simultaneously have action of modifying the taste; the binder is selected from one or more of carboxymethylcellulose sodium, methylcellulose, povidone, tragacanth, acacia, the binder can have simultaneously suspension promotion; the sweetener is selected from sucrose, glucose, Aspartame or Steviosin.

The more preferred formulations according to the present invention are demonstrated in Examples.

The oseltamivir phosphate granules of the present invention are prepared by following steps:

1) drying oseltamivir phosphate, diluent and binder at 40-60° C. for 4 hours, crushing and passing through 100 mesh sieve;

2) exactly weighing oseltamivir phosphate, diluent and binder in formation amount, optically adding edible flavouring essence, mixing uniformly by equivalent increase method to give a mixture powder;

3) preparing soft material with 30-55 v/v % ethanol aqueous solution, passing through 14 mesh sieve and pelletizing;

4) drying the wet granules at 45-60° C. completely, finishing the granules by passing through 14 mesh sieve to give dried granules;

5) passing the dried granules through No. 5 sieve to remove fine powders, determining the content of the primary pharmaceutical of the granules and moisture, defining package amount, packing; or mixing the dried granules and edible pigments uniformly and packing to give oseltamivir phosphate granules.

The granules of the present invention are in the form of unit dose, they can be packed in a bottle or in a bag. Per bottle or bag contains 0.6-6 g granules. Preferably, the formulation is packed using aluminum and plastic composite film, per bag contains 0.6-6 g granules.

It has been found by testing the obtained granules that the granules of the present invention (especially the granules prepared by the preferred formulation) have following advantages:

(1) appropriate degree of tightness, good fluidity, exact package amount, uniform content, and high release degree;

(2) good stability of granules, long storage time;

(3) the granules is water-soluble; the resultant aqueous solution is clear and transparent and good taste; the children exhibits high compliableness to it, and meanwhile the bioavailability of oseltamivir phosphate is enhanced;

(4) the granules is convenient in administration, dissolves immediately in mouth, it can be taken by buccal or with water;

(5) the production process is simple and low cost;

(6) the determination of administration dose of children's patients is easy.

EMBODIMENTS

Example 1

Preparation of Oseltamivir Phosphate Granules in 15 mg Specification

| Ingredients | Weight |
| --- | --- |
| oseltamivir phosphate (based on dried product) | 19.7 g (containing 15 g of oseltamivir) |
| Sucrose | 568.3 g |
| Povidone k30 | 12 g |
| Total amount | 600 g |

Oseltamivir phosphate and adjuvants were crushed to pass through 100 mesh sieve. oseltamivir phosphate, povidone k30 and sucrose were weighed exactly in an amount in the formulation, and mixed uniformly by equivalent increase method; the mixture was prepared into a soft material with 40 v/v % ethanol aqueous solution, passed through 14 mesh sieve and pelletized. The wet granules were dried at 45-60° C. in an oven, finished by passing through 14 mesh sieve, sieved using No. 5 sieve to remove fine powder. The content of the primary drug of the granules and moisture were determined, and the package amount was determined. The obtained granules were packed with aluminum plastic composite film into packages of 0.6 g/per unit dose, which contains 15 mg of oseltamivir.

The obtained granules can also be packed into unit package containing 30 mg or 45 mg of oseltamivir.

Example 2

Preparation of Oseltamivir Phosphate Granules in 15 mg Specification

| Ingredients | Weight |
| --- | --- |
| oseltamivir phosphate (based on dried product) | 19.7 g (containing 15 g of oseltamivir) |
| Sucrose | 968.3 g |
| Povidone k30 | 12 g |
| Total amount | 1000 g |

Oseltamivir phosphate and adjuvants were crushed to pass through 100 mesh sieve. oseltamivir phosphate, povidone k30 and sucrose were weighed exactly in an amount in the formulation, and mixed uniformly by equivalent increase method; the mixture was prepared into a soft material with 40 v/v % ethanol aqueous solution, passed through 14 mesh sieve and pelletized. The wet granules were dried at 45-60° C. in an oven, finished by passing through 14 mesh sieve, sieved using No. 5 sieve to remove fine powder. The content of the primary drug of the granules and moisture were determined, and the package amount was determined. The obtained granules were packed with aluminum plastic composite film into packages of 1.0 g/per unit dose, which contains 15 mg of oseltamivir.

The obtained granules can also be packed into unit package containing 30 mg or 45 mg of oseltamivir.

Example 3

Preparation of Oseltamivir Phosphate Granules in 25 mg Specification

| Ingredients | Weight |
| --- | --- |
| oseltamivir phosphate (based on dried product) | 32.83 g (containing 25 g of oseltamivir) |
| Sucrose | 947.17 g |
| Povidone | 20 g |
| Total amount | 1000 g |

The preparation method was described as in Example 1. The obtained granules were packed with aluminum plastic composite film into packages of 1 g/per unit dose, which contains 25 mg of oseltamivir.

The obtained granules can also be packed into unit package containing 15 mg, 30 mg or 45 mg of oseltamivir.

Example 4

Preparation of Oseltamivir Phosphate Granules in 25 mg Specification

| Ingredients | Weight |
| --- | --- |
| oseltamivir phosphate (based on dried product) | 39.4 g (containing 30 g of oseltamivir) |

| Ingredients | Weight |
| --- | --- |
| Sucrose | 1136.6 g |
| Povidone | 24 g |
| Total amount | 1200 g |

The preparation method was described as in Example 1. The obtained granules were packed with aluminum plastic composite film into packages of 1.2 g/per unit dose, which contains 25 mg of oseltamivir.

The obtained granules can also be packed into unit package containing 15 mg, 30 mg or 45 mg of oseltamivir.

Example 5

Preparation of Oseltamivir Phosphate Granules in 25 mg Specification

| Ingredients | Weight |
| --- | --- |
| oseltamivir phosphate (based on dried product) | 59.1 g (containing 45 g of oseltamivir) |
| Sucrose | 1704.9 g |
| Povidone | 36 g |
| Total amount | 1800 g |

The preparation method was described as in Example 1. The obtained granules were packed with aluminum plastic composite film into packages of 1 g/per unit dose, which contains 25 mg of oseltamivir.

The obtained granules can also be packed into unit package containing 15 mg, 30 mg, 45 mg, 60 mg or 75 mg of oseltamivir.

Example 6

Preparation of Oseltamivir Phosphate Granules in 25 mg Specification

| Ingredients | Weight |
| --- | --- |
| oseltamivir phosphate (based on dried product) | 78.8 g (containing 60 g of oseltamivir) |
| Sucrose | 2273.2 g |
| Povidone | 48 g |
| Total amount | 2400 g |

The preparation method was described as in Example 1. The obtained granules were packed with aluminum plastic composite film into packages of 1 g/per unit dose, which contains 25 mg of oseltamivir.

The obtained granules can also be packed into unit package containing 15 mg, 30 mg, 45 mg, 60 mg, 75 mg or 90 mg of oseltamivir.

Example 7

Preparation of Oseltamivir Phosphate Granules in 25 mg Specification

| Ingredients | Weight |
| --- | --- |
| oseltamivir phosphate (based on dried product) | 98.49 g (containing 75 g of oseltamivir) |
| Sucrose | 2841.51 g |
| Povidone | 60 g |
| Total amount | 3000 g |

The preparation method was described as in Example 1. The obtained granules were packed with aluminum plastic composite film into packages of 1 g/per unit dose, which contains 25 mg of oseltamivir.

The obtained granules can also be packed into unit package containing 15 mg, 30 mg, 45 mg, 60 mg, 75 mg, 90 mg or 150 mg of oseltamivir.

Example 8

Preparation of Oseltamivir Phosphate Granules in 25 ng Specification

| Ingredients | Weight |
| --- | --- |
| oseltamivir phosphate (based on dried product) | 197.2 g (containing 150 g of oseltamivir) |
| Sucrose | 5683.6 g |
| Povidone | 120 g |
| Total amount | 6000 g |

The preparation method was described as in Example 1. The obtained granules were packed with aluminum plastic composite film into packages of 1 g/per unit dose, which contains 25 mg of oseltamivir.

The obtained granules can also be packed into unit package containing 15 mg, 30 mg, 45 mg, 60 mg, 75 mg, 90 mg or 150 mg of oseltamivir.

Example 9

Preparation of Oseltamivir Phosphate Granules in 15 mg Specification

| Ingredients | Weight |
| --- | --- |
| oseltamivir phosphate (based on dried product) | 32.83 g (containing 25 g of oseltamivir) |
| Sucrose | 947.17 g |
| Carboxymethylcellulose sodium | 20 g |
| Total amount | 1000 g |

Oseltamivir phosphate and adjuvants were crushed to pass through 100 mesh sieve. oseltamivir phosphate, carboxymethylcellulose sodium and sucrose were weighed exactly in an amount in the formulation, and mixed uniformly by equivalent increase method; the mixture was prepared into a soft material with 40% ethanol aqueous solution, passed through 14 mesh sieve and pelletized. The wet granules were dried at 45-60° C. in an oven, finished by passing through 14 mesh sieve, sieved using No. 5 sieve to remove fine powder. The content of the primary drug of the granules and moisture were determined, and the package amount was determined. The obtained granules were packed with aluminum plastic composite film into packages of 1.0 g/per unit dose, which contains 25 mg of oseltamivir.

The obtained granules can also be packed into unit package containing 15 mg, 30 mg, 45 mg, 50 mg or 75 mg of oseltamivir.

Example 10

Preparation of Oseltamivir Phosphate Granules in 25 mg Specification

| Ingredients | Weight |
| --- | --- |
| oseltamivir phosphate (based on dried product) | 32.83 g (containing 25 g of oseltamivir) |
| Sucrose | 947.17 g |
| Methylcellulose sodium | 20 g |
| Total amount | 1000 g |

Oseltamivir phosphate and adjuvants were crushed to pass through 100 mesh sieve. oseltamivir phosphate, methylcellulose sodium and sucrose were weighed exactly in an amount in the formulation, and mixed uniformly by equivalent increase method; the mixture was prepared into a soft material with 40 v/v % ethanol aqueous solution, passed through 14 mesh sieve and pelletized. The wet granules were dried at 45-60° C. in an oven, finished by passing through 14 mesh sieve, sieved using No. 5 sieve to remove fine powder. The content of the primary drug of the granules and moisture were determined, and the package amount was determined. The obtained granules were packed with aluminum plastic composite film into packages of 1.0 g/per unit dose, which contains 25 mg of oseltamivir.

The obtained granules can also be packed into unit package containing 15 mg, 30 mg, 45 mg, 50 mg or 75 mg of oseltamivir.

Example 11

Preparation of Oseltamivir Phosphate Granules in 150 mg Specification

| Ingredients | Weight |
| --- | --- |
| oseltamivir phosphate (based on dried product) | 197.2 g (containing 150 g of oseltamivir) |
| Sucrose | 752.8 g |
| Povidone | 50 g |
| Total amount | 1000 g |

The preparation method was described as in Example 1. The obtained granules were packed with aluminum plastic composite film into packages of 1 g/per unit dose, which contains 150 mg of oseltamivir.

The obtained granules can also be packed into unit package containing 15 mg, 30 mg, 45 mg, 60 mg, 75 mg, or 90 mg of oseltamivir.

Example 12

Test of Solubility and Dispersibility of Oseltamivir Phosphate

When the granules obtained in Example 1 were prepared with water into a solution containing 5 mg/ml of oseltamivir, the pH was tested to be about 5.4, the solution was neutral to weakly acid solution, had no stimulus to human body, had good taste, and was in favor of use of patients.

According to the requirements of Chinese Pharmacopoeia, 2005 edition, Part 2, Annex IX B, the second method (double sieving method), the sum of No. 1 oversize product and No. 5 undersize product should not exceed 15% of test samples. The test results showed that aforesaid granules samples were all in conformity with the requirements of Chinese Pharmacopoeia to completely guarantee the uniformity of the particle size of the granules, so that the quality of the granules was not influenced by damp caking or breaking during transportation and storage.

10 g of said granules samples was added with 200 ml of hot water, stirred for 5 min, the solubility of the samples was observed. The test results showed that the samples dissolved completely, no foreign matters appeared, in conformity with the requirements of Chinese Pharmacopoeia, 2005 edition, Part 2, Annex IN. The prepared soluble oseltamivir phosphate granules can completely disperse or dissolve in water, so as to ensure the bioavailability of the granules and be convenient for the use of patients.

What is claimed is:

1. Oseltamivir phosphate granules, comprising:

| oseltamivir phosphate at | 3.28 wt. %; |
| --- | --- |
| sucrose at | 94.72 wt. %; and |
| povidone k30 at | 2.00 wt. %. |

2. The oseltamivir phosphate granules of claim 1, wherein per unit dose the oseltamivir phosphate granules contain 15 mg or 25 mg of oseltamivir.

3. A method for preparing the oseltamivir phosphate granules of claim 1, comprising:
drying the oseltamivir phosphate, the sucrose, and the povidone k30 at 40-60° C. for 4 hours to form dried components;
crushing the dried components through a 100 mesh sieve;
exactly weighing the oseltamivir phosphate, the sucrose, and the povidone k30 in formulation amount, optionally adding an edible flavoring essence;
mixing uniformly by equivalent increase method to form a mixture powder;
adding 30-55 v/v % of ethanol aqueous solution to the mixture powder to form a soft material;
passing the soft material through a 14 mesh sieve to form a pellet of wet granules;
drying the pellet of wet granules at 45-60° C. completely and passing through a 14 mesh sieve to form dried granules; and
sieving the dried granules to remove fine powder;
determining the content of a primary drug in the granules and moisture; and determining package amount, packing or mixing the dried granules and edible pigment uniformly and packing to prepare the oseltamivir phosphate granules.

4. Oseltamivir phosphate granules, comprising:

| | | |
|---|---|---|
| oseltamivir phosphate at | 1.97 | wt. %; |
| sucrose at | 96.83 | wt. %; and |
| povidone k30 at | 1.20 | wt. %. |

5. The oseltamivir phosphate granules of claim 4, wherein per unit dose the oseltamivir phosphate granules contain 15 mg or 25 mg of oseltamivir.

6. A method for preparing the oseltamivir phosphate granules of claim 4, comprising:

drying the oseltamivir phosphate, the sucrose, and the povidone k30 at 40-60° C. for 4 hours to form dried components;

crushing the dried components through a 100 mesh sieve;

exactly weighing the oseltamivir phosphate, the sucrose, and the povidone k30 in formulation amount, optionally adding an edible flavoring essence;

mixing uniformly by equivalent increase method to form a mixture powder;

adding 30-55 v/v % of ethanol aqueous solution to the mixture powder to form a soft material;

passing the soft material through a 14 mesh sieve to form a pellet of wet granules;

drying the pellet of wet granules at 45-60° C. completely and passing through a 14 mesh sieve to form dried granules; and sieving the dried granules to remove fine powder;

determining the content of a primary drug in the granules and moisture; and determining package amount, packing or mixing the dried granules and edible pigment uniformly and packing to prepare the oseltamivir phosphate granules.

7. Oseltamivir phosphate granules, comprising:

| | | |
|---|---|---|
| oseltamivir phosphate at | 3.28 | wt. %; |
| sucrose at | 94.72 | wt. %; and |
| carboxymethylcellulose sodium at | 2.00 | wt. %. |

8. The oseltamivir phosphate granules of claim 7, wherein per unit dose the oseltamivir phosphate granules contain 15 mg or 25 mg of oseltamivir.

9. A method for preparing the oseltamivir phosphate granules of claim 7, comprising:

drying the oseltamivir phosphate, the sucrose, and the carboxymethylcellulose sodium at 40-60° C. for 4 hours to form dried components;

crushing the dried components through a 100 mesh sieve;

exactly weighing the oseltamivir phosphate, the sucrose, and the carboxymethylcellulose sodium in formulation amount, optionally adding an edible flavoring essence;

mixing uniformly by equivalent increase method to form a mixture powder;

adding 30-55 v/v % of ethanol aqueous solution to the mixture powder to form a soft material;

passing the soft material through a 14 mesh sieve to form a pellet of wet granules;

drying the pellet of wet granules at 45-60° C. completely and passing through a 14 mesh sieve to form dried granules; and sieving the dried granules to remove fine powder;

determining the content of a primary drug in the granules and moisture; and determining package amount, packing or mixing the dried granules and edible pigment uniformly and packing to provide the oseltamivir phosphate granules.

10. Oseltamivir phosphate granules, comprising:

| | | |
|---|---|---|
| oseltamivir phosphate at | 3.28 | wt. %; |
| sucrose at | 94.72 | wt. %; and |
| methylcellulose sodium at | 2.00 | wt. %. |

11. The oseltamivir phosphate granules of claim 10, wherein per unit dose the oseltamivir phosphate granules contain 15 mg or 25 mg of oseltamivir.

12. A method for preparing the oseltamivir phosphate granules of claim 10, comprising:

drying the oseltamivir phosphate, the sucrose, and the methylcellulose sodium at 40-60° C. for 4 hours to form dried components;

crushing the dried components through a 100 mesh sieve;

exactly weighing the oseltamivir phosphate, the sucrose, and the methylcellulose sodium in formulation amount, optionally adding an edible flavoring essence;

mixing uniformly by equivalent increase method to form a mixture powder;

adding 30-55 v/v % of ethanol aqueous solution to the mixture powder to form a soft material;

passing the soft material through a 14 mesh sieve to form a pellet of wet granules;

drying the pellet of wet granules at 45-60° C. completely and passing through a 14 mesh sieve to form dried granules; and sieving the dried granules to remove fine powder;

determining the content of a primary drug in the granules and moisture; and determining package amount, packing or mixing the dried granules and edible pigment uniformly and packing to prepare the oseltamivir phosphate granules.

* * * * *